United States Patent [19]
Arnott

[11] Patent Number: 5,766,218
[45] Date of Patent: Jun. 16, 1998

[54] SURGICAL BINDING DEVICE AND METHOD OF USING SAME

[75] Inventor: Richard J. Arnott, Pittsburgh, Pa.

[73] Assignee: Metamorphic Surgical Devices, Inc., Pittsburgh, Pa.

[21] Appl. No.: 724,195

[22] Filed: Oct. 1, 1996

[51] Int. Cl.$^6$ .................................................. A61B 17/04
[52] U.S. Cl. ............................ 606/151; 606/74; 606/78; 606/223; 24/16 PB; 24/484
[58] Field of Search ............................ 606/151, 78, 74, 606/213, 215, 222, 223; 24/16 PB, 17 AP, 484, 30.5 P

[56] References Cited

U.S. PATENT DOCUMENTS

| | | | |
|---|---|---|---|
| 2,987,062 | 6/1961 | Ellison | 606/74 |
| 3,570,497 | 3/1971 | Lemole | 606/74 |
| 3,993,109 | 11/1976 | Fortsch | 140/123.6 |
| 4,119,091 | 10/1978 | Patridge | 606/74 |
| 4,170,990 | 10/1979 | Baumgart et al. | 606/78 |
| 4,263,904 | 4/1981 | Judet | 606/74 |
| 4,665,906 | 5/1987 | Jervis | 128/92 YN |
| 4,730,615 | 3/1988 | Sutherland et al. | 128/335 |
| 4,813,416 | 3/1989 | Pollak et al. | 128/335 |
| 5,002,563 | 3/1991 | Pyka et al. | 606/78 |
| 5,190,546 | 3/1993 | Jervis | 606/78 |
| 5,290,289 | 3/1994 | Sanders et al. | 606/61 |
| 5,366,461 | 11/1994 | Blasnik | 606/151 |
| 5,383,882 | 1/1995 | Buess et al. | 606/157 |
| 5,417,702 | 5/1995 | Hempel | 606/151 |
| 5,437,685 | 8/1995 | Blasnik | 606/151 |
| 5,549,619 | 8/1996 | Peters et al. | 606/151 |
| 5,551,871 | 9/1996 | Besselink et al. | 606/78 |
| 5,597,378 | 1/1997 | Jervis | 606/78 |

OTHER PUBLICATIONS

Harry L. LeVeen, M.D. et al.; "Nylon–Band Chest Closure"; *Arch Surg*; vol. 96; Jan. 1968; pp. 36–39.

Darel E. Hodgson et al.; "Shape Memory Alloys"; *Metals Handbook*; Tenth Edition; vol. 2 Properties and Selection: Nonferrous Alloys and Special–Purpose Materials; pp. 897–902.

*An Introduction to Martensite and Shape Memory*; pp. 9–19.

*Primary Examiner*—Gary Jackson
*Attorney, Agent, or Firm*—Webb Ziesenheim Bruening Logsdon Orkin & Hanson, P.C.

[57] ABSTRACT

A binding device and method of use for providing a compressive force across tissue boundaries to promote healing. The binding device includes a strap adapted to form a loop about injured tissue and a tension member attached to the strap, wherein the tension member maintains a predetermined stress level in the loop which compresses the edges of the tissue together to foster healing. The tension member is preferably a shape memory effect alloy, such as nitinol, a nickel-titanium alloy. The binding device also includes a one-way locking mechanism which keeps the strap in a loop.

14 Claims, 5 Drawing Sheets

SURGICAL BINDING DEVICE AND METHOD OF USING SAME

1. TECHNICAL FIELD

The present invention relates to a binding device, and more particularly, to a surgical binding device to repair an incision, tear, break or other wound by holding the edges of affected tissue in contact and applying a compressive force thereto.

2. BACKGROUND OF THE INVENTION

Sutures are used to draw together and hold tissue boundaries of an incision, tear, break or other wound (injury) in contact to stimulate the healing process. Such surgical repair situations are quite broad in nature and have motivated the development of sutures of various materials and cross-sectional dimensions. Such materials may be characterized as either absorbable or nonabsorbable.

Bone Fracture Repair

Bone fracture repair is characterized by two necessary and distinct processes: fixation and compression. Fixation immobilizes break boundaries in close proximity. Compression affects the quality of the new bone laid down at the union. Fixation is a static process, compression a dynamic one. Compression is dynamic because it must be maintained during dimensional redefinition occurring at the break boundary that is a natural component of healing.

Most currently used devices, such as screws, plates, rods, etc. adequately address bone fixation. Manufacturers of such devices acknowledge the importance of compression, but continue to address compression in a static fashion. Consequently, compression across a break boundary decreases during the healing process. Typically, within the first two weeks, it will decrease to approximately 50% of initial force; within the first two months it will have decreased to 30% of initial force.

A bone plate, which spans a fracture, fixes break boundaries relative to each other and provides a sliding action during attachment to create an initial compressive force. The sliding action is caused by the interface of the conical under surface of the screw head and the vertical wall of the screw hole in the plate.

Screws are often used to fix the boundaries of an oblique fracture. Again, the need for compression, as a necessary component for proper healing, has been demonstrated and is acknowledged in screw design which utilizes two sets of threads, one at the tip and one just below the head. The width of the threads near the tip is narrower than near the head. The pitch of the threads in each is the same magnitude, but reversed in direction. A hole of adequate diameter is drilled into the bone so that the threads at the tip may pass through the initial bone fragment without threading. As the tip threads bite into the second bone fragment, they pull the screw into it. After reaching an adequate depth, the threads near the head bite into the initial fragment. As a result of the reverse pitch, the bone fragment boundaries are pulled together by further turning of the screw. In this way, the break boundaries are drawn together producing a greater initial compressive force than a screw with continuous threads of constant pitch.

Thoracic Surgery

Monofilament stainless steel suture wire, such as that made by American Cyanamid, is frequently used for various procedures in which large forces are required to fix tissue boundaries relative to each other. This suture consists of an 18 inch length of 0.030 inch diameter circular stainless steel wire with a curved needle crimped to one end. The needle is of larger diameter than the stainless steel wire.

As an example of where the suture is currently used, consider open chest surgical procedures, such as coronary valve replacement or coronary artery bypass. These procedures require the sternum (breast bone) to be split down the middle from manubrium to ensiform and then spread apart for adequate visualization and surgical access. Splitting is accomplished with a reciprocating saw. The two halves of the sternum created by sawing are then spread apart (by a rib spreader) to provide the surgeon with visualization of and access to the thoracic cavity. On completion of the open chest procedure, the two halves of the sternum are fixed relative to each other by the monofilament stainless steel sutures. Typically, five sutures are used.

Though the monofilament stainless steel is somewhat inflexible, each suture is passed around both halves of the divided sternum. The sutures may be positioned between ribs in the corresponding intercostal spaces on both left and right sides of the sternum, and inserted through the cartilage attaching corresponding ribs on both left and right sides to the sternum. Alternatively, the sutures may be passed through the bone of both halves of the divided sternum. The curved needle at one end of the suture is used to pierce the cartilage or bone. The ends of the suture are brought to the anterior or front side of the sternum. The needle is then cut from the suture and the ends of the suture are twisted to pull together and fix the halves of the sternum. Any extra wire is then cut and the twisted ends folded over into the sternum.

This is a very imprecise process that has numerous problems attributable to the stainless steel suture. "Although the soft bone may be pierced with a cutting needle, it is sometimes necessary to drill holes. The wire may later erode through the skin, which lies close to the sternum, and can cause a chronic draining sinus or osteomyelitis of the sternum. Anchorage in the cancellous bone is insecure and separation of the sternum may occur if the wire cuts through the thin anterior and posterior sternal tables." Harry L. LeVeen, M.D. et al., *Nylon-Band Chest Closure, Arch Surg*, Vol. 96, Jan. 1968, p. 36.

The monofilament stainless steel wire suture has further disadvantages. For example, twisting the wire increases the cold work in the wire, making it more brittle and increasing the likelihood that it will break. Breaking necessitates that a new suture be installed.

Additionally, initial compressive force across the sternum halves generated by twisting the wire can become very large. Because the wire has a small diameter, anatomical structures may experience excessive localized pressure resulting in damage. For example, bone may fracture or experience necrosis; cartilage may tear, etc. Compression is necessary for quality bone reformation and a solid union of the sternal halves. The width of the sternum tends to decrease due to the nature of the healing process. The wire suture cannot respond to this dimensional change and consequently does not maintain compression across the facing boundaries of the divided sternum during the healing process. Thus, applied pressure decreases with time.

Furthermore, the wire of the prior art can kink under the sternum, out of sight of the surgeon, greatly increasing the possibility of a wire failure. Post surgery, the stainless steel wire is prone to break during any episode that further increases the cold work in the wire making it more brittle.

It is not uncommon for a patient to experience a buildup of fluids in the chest that must be cleared. The natural means is coughing. Coughing forces the chest to expand, increasing the cold work in the wire. The wire may then break, necessitating a corrective surgical procedure. Post surgery, the twisted sutures can be felt as a ridges under the skin covering the sternum. They are a constant reminder to the patient of the intricate and physically traumatizing surgical procedure. They act as a continuing source of psychological trauma. They also act as heat sinks, causing augmented cooling of covering tissue, perhaps to a discomforting excess. As life expectancy increases, it is likely that a patient may undergo a repeat procedure. Pre-existing sutures must be dealt with. Usually, the surgeon cuts the wire suture across the anterior of the sternum. If possible, he then slides the suture from around the sternum. Frequently, however, this is not possible due to in-growth into surrounding tissue. Consequently, the surgeon must cut the suture material behind the sternum during the cutting of the sternum with the sternotomy saw which cuts with a reciprocating rotational motion. This can pose an added risk to the patient as the saw can snag on the suture. The problem is exacerbated as the heart can adhere to the under side of the sternum as a consequence of a previous open chest procedure.

Finally, operating room time is expensive, as much as $80 per minute. The current method of joining the sternum is a cumbersome and archaic technique, which excessively increases operating time and associated risk to the patient.

Recently, Pioneer Laboratories introduced a one millimeter stainless steel cable to address issues of stiffness and weakening associated with the monofilament stainless steel wire used in sternotomy closures discussed above. This system uses an expensive and cumbersome tool to tighten the cable to a designated tension and then crimp the ends. It is still prone to the other problems associated with a shape that does not distribute initial compressive forces.

Alternatively, other existing prior art advocated the use of self-locking plastic bands for median sternotomy closure which are positioned in the intercostal spaces and around the entire width of the sternum and reported that only two to three bands were required. Pfizer Hospital Products Group, Inc. disclosed, in U.S. Pat. No. 4,730,615, a band of a biocompatible metal coated with a biocompatible polymer along parts of its length. Recently, Sterna-Band has marketed a stainless steel band for sternotomy closures which is described in U.S. Pat. No. 5,366,461. Sterna-Band's design basically addresses the issue of fixation stability by providing a wider device. No tool is provided for controlling initial tension at installation.

Though sternotomy closure deals with bone healing, each system described basically addresses only fixation of the two sternal halves relative to each other. The issue of compression is not directly addressed. This component of bone healing is recognized only in the objective of each system to establish an initial large compressive force. As stated above, this force immediately begins to diminish in the initial phase of bone healing, but such large forces, in themselves, are detrimental relative to the concentrated forces experienced proximal to the wires, whether monofilament or cable. While the stainless steel system provides some stability, it is deficient as a means to establish a known initial force and never reconciles the need for continuous compressive force.

Furthermore, such physiological activities as sighing and coughing contribute to degeneration of both the devices and the sternum in that expansive forces increase local pressure on the sternum and also detrimentally stress the closure device. Therefore, results include degeneration of sternal tissue and stretching/breaking of the closure device.

Abdominal Surgery

Monofilament stainless steel sutures have also been used ineffectively to relieve expansive stress across primary sutures closing long incisions. This technique is quite prevalent in abdominal surgical procedures. Usually the secondary stainless steel suture set spans the width of the abdomen, encompassing the primary sutures positioned vertically along the abdomen. The stainless steel sutures are placed percutaneously under or behind the abdominal muscle wall. The ends are exposed and brought together in the approximate center of the abdominal surface and twisted to pull abdominal tissues together, as in the sternum procedure.

Many of the same problems noted earlier persist. The primary problem, however, is the effect of forces generated by the suture on abdominal tissue. Because initial forces created by twisting the wire can become very large, flesh and muscle through which the wire passes experience very large local forces, sufficient to tear/cut through them over time. Any activity which causes the abdomen to expand exacerbates such tearing/cutting.

Beyond the damage to those tissues, the primary sutures are then exposed to elevated expansive forces, causing them to loosen and tear, allowing the incision edges to separate. The patient can then experience increased scarring and augmented probability of infection.

It is thus an object of this invention that the binding device is easily and quickly installed and provides feedback to the physician on the stress he has produced in the binding device during the installation. It is a further object of this invention that the binding device has a broad cross section to moderate local forces that can damage tissue. It is another object that the binding device be flexible so that it can mold around tissue. A further object is to have a sharpened end, either of the same material or another harder material, that can pierce through tissue, such as cartilage or soft bone. It is a further object that the binding device predictably controls the maximum force that tissue in intimate contact with the device experiences. The device stretches within a desired range at a known or programmable force level, effectively resists stretching beyond that range and then is capable of returning to its prestretched length while generating a known force. It is a further object of the invention that the binding device applies a substantially constant compressive force during the healing process, even as tissue boundaries modify. It is a further object that the binding device dissipate stress resulting from expansive forces occurring across the binding device due to physiological events. The binding device should allow a certain amount of expansion for dissipation of stress, and then, after reaching a limit, prevent additional expansion. The binding device then returns to its prestressed dimension.

SUMMARY OF THE INVENTION

The above objects are achieved by a binding device in accordance with the present invention. The binding device comprises a strap and a tension member attached to the strap, wherein the tension member maintains tension in the strap to maintain the tissue together. The tension member may be a shape memory effect alloy, preferably a shape memory effect alloy selected from the group consisting of nitinol, Cu-Zn-Al and Cu-Al-Ni. The binding device may further comprise a one-way locking mechanism for securing the strap in the form of a loop.

One embodiment of the present invention is a surgical binding device comprising a self-locking strap adapted to be looped through adjacent edges of tissue and tightened for holding the tissue in close proximity with a tension member attached to the strap. The tension member maintains a substantially constant predetermined tension level in the strap to maintain the tissue in close proximity. Further, the strap may comprise a frictional surface for contacting the tissue and preventing translation therebetween. The strap may be provided with a piercing end for insertion through the tissue. The piercing end may include a removable needle. Additionally, the strap may include a base opposite the piercing end and a tie portion. The base is adapted to irreleasably receive the piercing end and the tie portion to form a tightenable loop. The device may further comprise a limiting mechanism for limiting the force applied to the tension member when the strap is tightened. The limiting mechanism comprises limiting tabs on one end of the tie portion and limiting holes on one end of the base, wherein the limiting tabs coact with the limiting holes to limit movement of the tie portion relative to the base.

Also disclosed is a method of binding together injured tissue under a compressive force to promote healing, comprising the steps of drawing together in close proximity opposing edges of injured tissue by tightening a strap which forms a loop about the injured tissue and tightening the strap so that a tension member within the strap exerts a substantially constant tension within the strap to maintain the tissue in close proximity.

Still other objects and advantages of the present invention will become readily apparent to those skilled in the art from the following detailed description, wherein only the preferred embodiments of the invention are shown and described, simply by way of illustration of the best mode contemplated of carrying out the invention. As will be realized, the invention is capable of other and different embodiments, and the specific details are capable of modifications in various obvious respects, all without departing from the present invention. Accordingly, the drawings and description are to be regarded as illustrative in nature, and not as restrictive.

DETAILED DESCRIPTION OF THE INVENTION

Figures 1, 2:
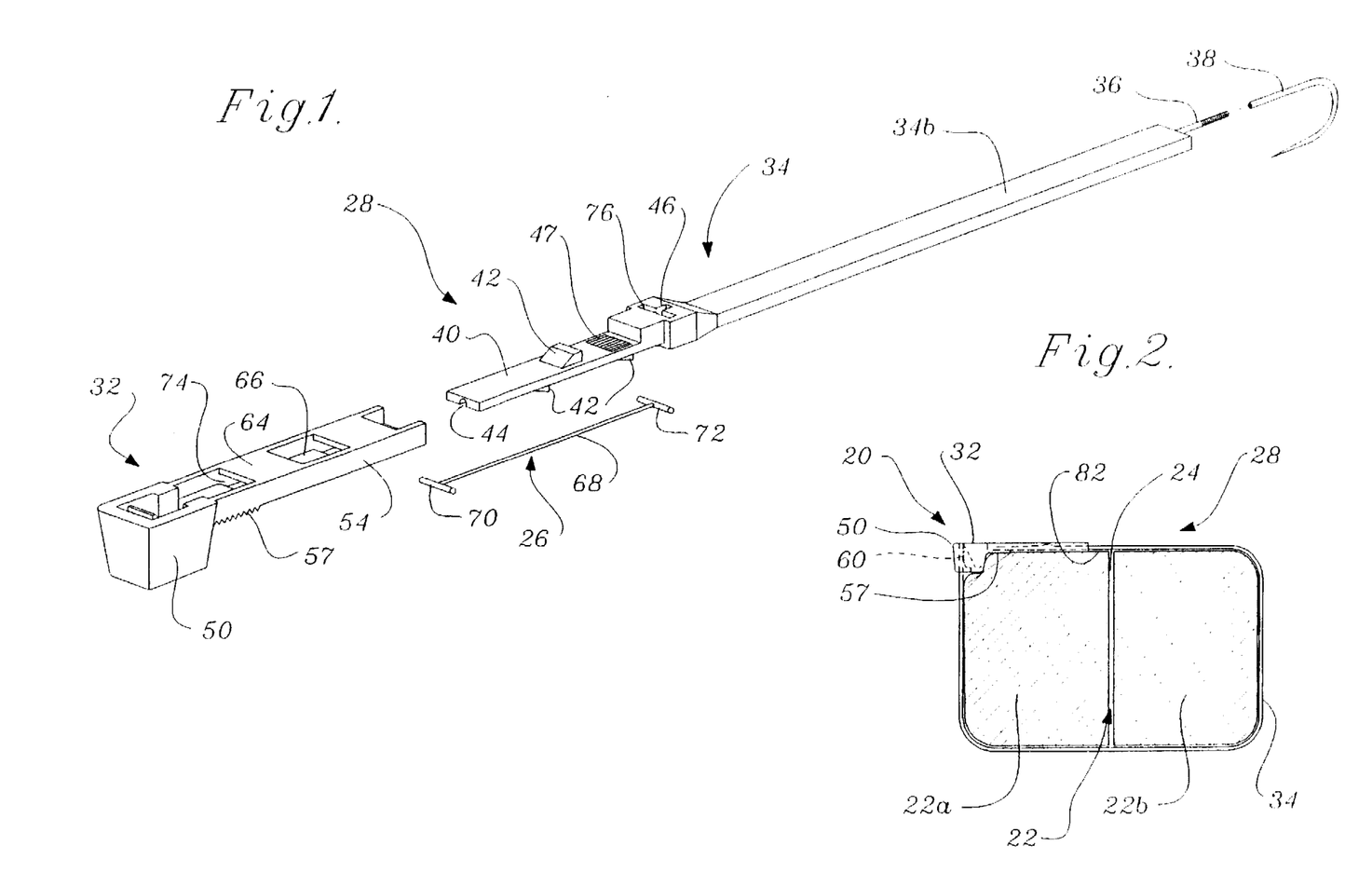
FIG. 1 is an exploded perspective view depicting a surgical binding device constructed in accordance with the present invention.
FIG. 2 is a partial sectional view of the surgical binding device of the invention applied to a split sternum.

FIGS. 1 and 2 illustrate a binding device 20 constructed in accordance with the present invention for preferred use applied to rejoin a split sternum 22 by fixing and compressing the halves 22a, 22b to promote healing.

The present invention is provided with a tension member 26, preferably in the form of a shape memory effect alloy, attached to a strap 28 of binding device 20. During use, as depicted in FIG. 2, tightening of strap 28 into a loop stretches tension member 26 to a point 30 on the stress-strain curve depicted in (a) of FIG. 3. Thus, tension member 26 exerts a substantially constant force or tension level within strap 28 which compresses a tissue boundary 24 to promote healing. This compressive force is substantially constant even after healing begins, resulting in construction of the tissue boundary 24 and/or expansive forces are applied, such as coughing.

Binding device 20 in accordance with the present invention comprises a flexible plastic or nylon strap 28 having a base 32 and a tie portion 34 releasably attached to each other through tension member 26. The nylon or plastic strap 28 will conform to the sternum over time with no loss in the compressive force applied due to the tension member 26. Tie portion 34 has a broad cross section to moderate local forces that could otherwise damage tissue. Referring to FIGS. 1 and 4(a)–4(d), tie portion 34 is provided with a piercing end 36, which is a sharpened end and may be constructed of the same material as the tie portion. Preferably, however, piercing end 36 comprises a needle 38 that is beneficially shaped to aid in stitching up a wound. An example of a preferred needle 38 is a stainless steel suture needle that is fixedly attached, such as by crimping, to tie portion 34.

The opposite end of tie portion 34 comprises a tongue 40 having limit tabs 42. Further, a longitudinal channel 44 for receiving tension member 26 runs the entire length of tongue 40 and terminates at a rod catch opening 46. One surface 34a of tie 34 facing toward the interior of the loop has a plurality of ridges 48 perpendicular to the longitudinal length of tie 34. Ridges 48 aid in securing strap 28 to form a loop. At one end of tongue 40 opposite exposed end 40a, the surface 34b facing away from the interior of the loop has a color stripe 47 to indicate the tightness of binding device 20.

The base 32, referring to FIGS. 1, 2 and 5–7, is preferably a rigid material having at one end a head 50 with a cavity 52 joined to an opposing open end 54 by a longitudinal chamber 56. Base 32 also comprises contacting teeth 57 which form a friction engaging surface to prevent translation between base 32 and adjacent tissue. During use, a piercing end 36 and part of tie portion 34 are fed through cavity 52 and held in place by a locking mechanism 58, which is preferably a one-way locking mechanism which prevents removal of the tie once it has been inserted. Locking mechanism 58 secures tie portion 34 with a tang 59 having teeth 60 which interact with ridges 48, but similar locking systems may also be used.

Longitudinal chamber 56 is for receiving tongue 40 and is substantially perpendicular to cavity 52 and adjacent head 50. An inner wall 62 and an outer wall 64 of chamber 56 correspond to surface 32a facing the interior of the loop and second surface 32b facing the exterior of the loop, respectively. The interior dimensions of chamber 56 are greater than the exterior dimensions of tongue 40, allowing the tongue to be received within the chamber. Limit holes 66, formed within inner wall 62 and outer wall 64, interact with limit tabs 42 on tongue 40 to permit some longitudinal movement of the tongue within chamber 56. Limit tabs 42 are shaped, however, to catch on limit holes 66 to prevent the removal of tongue 40 from chamber 56 and to limit the stretching of tension member 26.

Referring to FIGS. 1 and 2, tension member 26 is attached to strap 28 and advantageously provides beneficial compressive force to aid in healing, while possibly allowing a limited amount of expansion from physiological events, such as coughing. Tension member 26 comprises a connecting member 68 having a first anchor 70 at one end and a second anchor 72 at the opposing end. To attach tension member to strap 28, each anchor 70, 72 is respectively fixed by anchor catches 74, 76 within base 32 and tie portion 34. Preferably, anchors 70, 72 are rods formed of a biocompatible metal.

Figure 3:
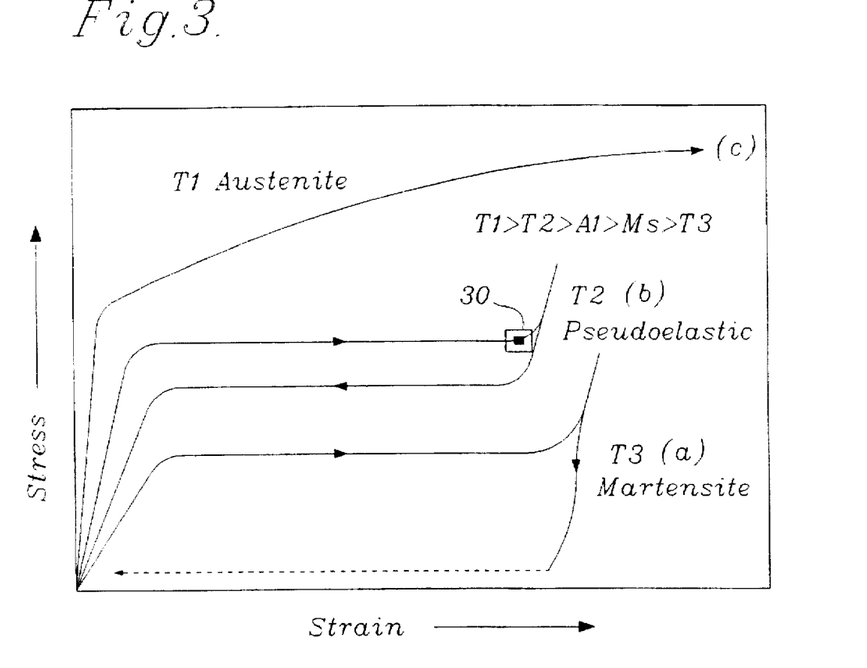
FIG. 3 is a graph representing the stress-strain curve of various states of a shape memory effect alloy.
Figure 4A:
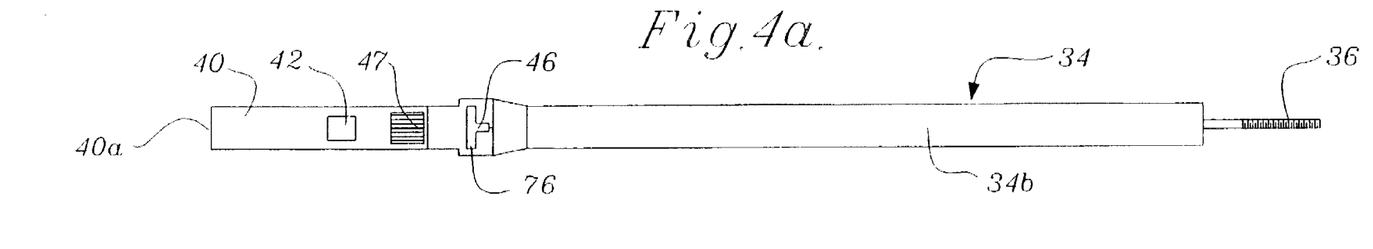
FIGS. 4(a)–4(d) are a top, side, bottom and end view, respectively, depicting the tie portion of the strap of the present invention.
Figure 4B:
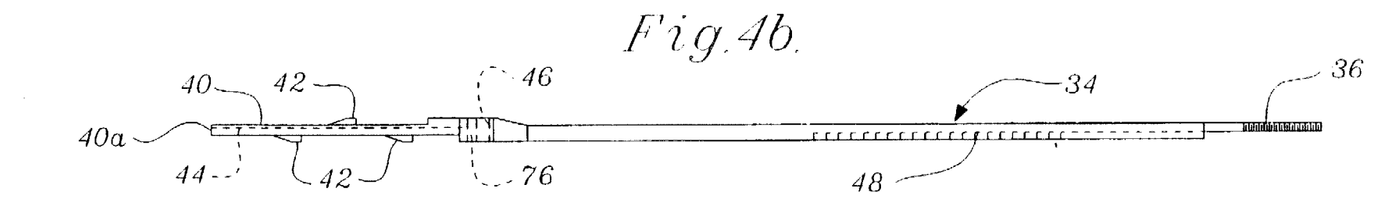
Figures 4C, 4D:
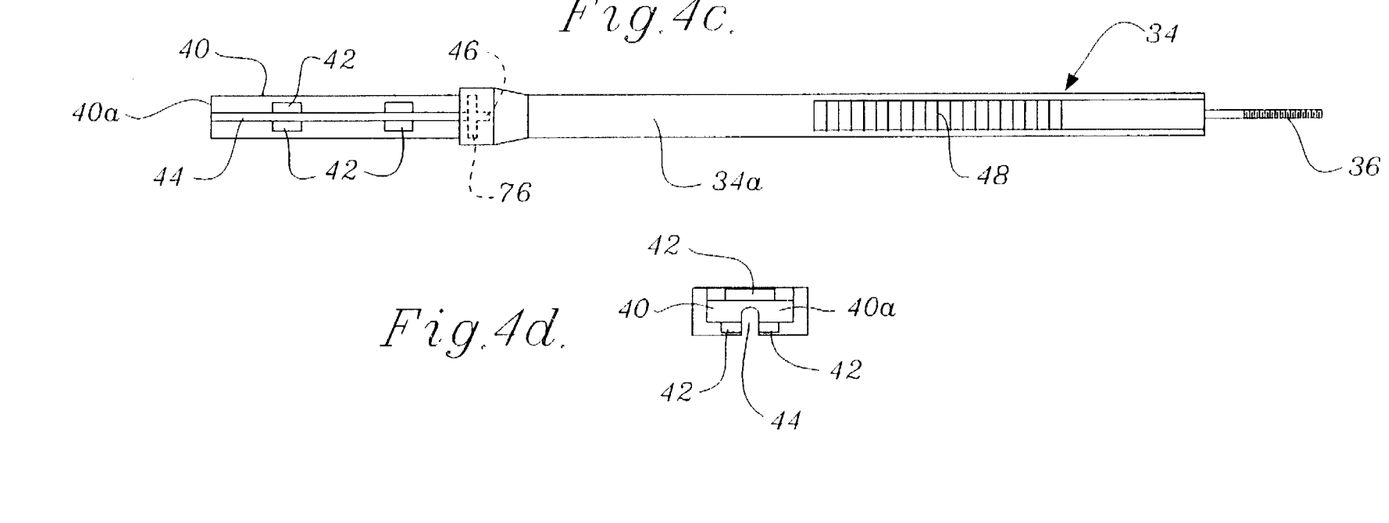
Figure 5A:
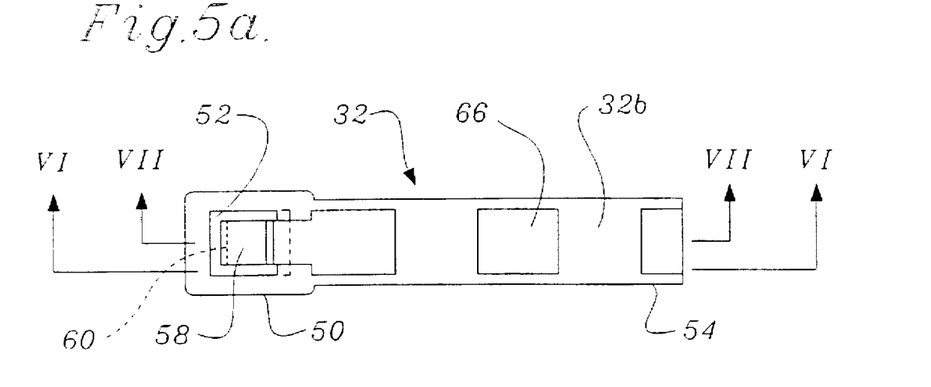
FIGS. 5(a)–5(b) are a top and end view, respectively, depicting the base of the strap of the present invention.
Figure 5B:
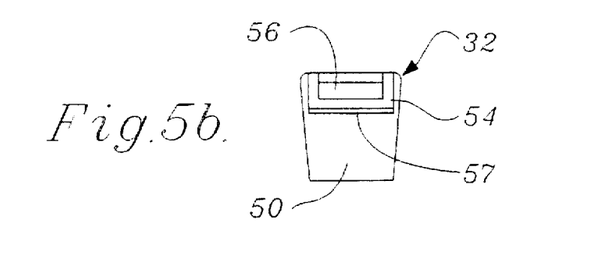
Figure 6:
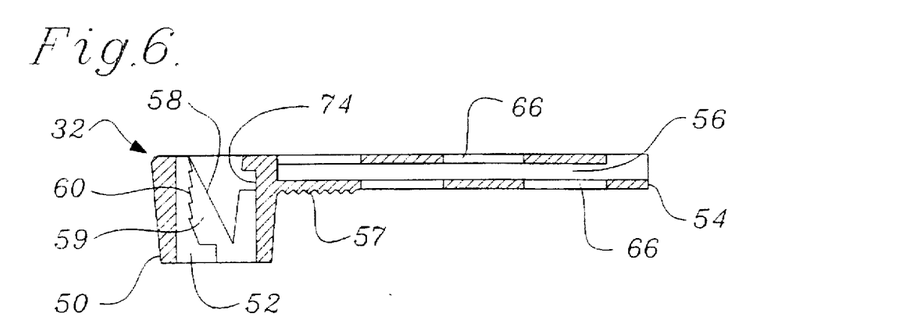
FIG. 6 is a sectional view of the base of the strap along line 6—6 in FIG. 5.
Figure 7:
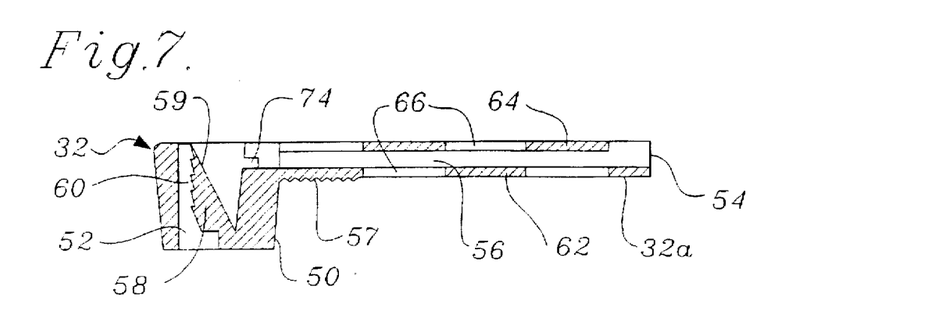
FIG. 7 is sectional view of the base of the strap along line 7—7 in FIG. 5.

Preferably, connecting member 68 is a shape memory effect alloy, wherein the connecting member 68 is pseudoelastic as shown in FIG. 3 to generate a substantially constant tension in the strap 28 over a range of motion. Connecting member 68 may be a single or multiple strands of material, a braided material or a strip of material. More preferably, connecting member 68 is a nickel-titanium alloy, such as nitinol, or a copper-base alloy, such as Cu-Zn-Al or Cu-Al-Ni.

Figure 8:
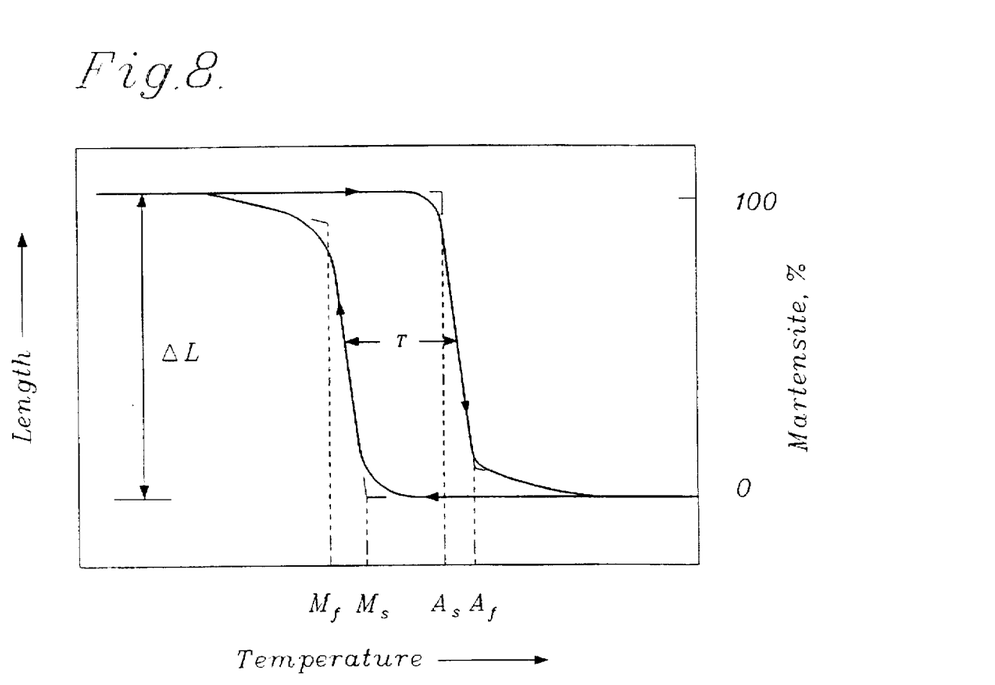
FIG. 8 is a graph depicting a typical transformation versus temperature curve for a shape memory effect alloy.

Shape memory effect alloys demonstrate the ability to substantially return to some previously defined shape or size, after being deformed, when subjected to an appropriate thermal procedure or when the deforming load is released. For example, nitinol can be taught to remember a shape in its austenite phase, deformed in its martensite phase, and then returned to the learned shape via a temperature-initiated transformation to the austenite phase. FIG. 8 depicts a graph of change in length versus change in temperature for a shape memory effect alloy under constant load (stress) as it is cooled and heated. FIG. 8 also shows the phase transformation from 0% martensite (or 100% austenite) to 100% martensite. The alloy starts out at a high temperature in the austenite phase (0% martensite). Deformation begins to occur at the martensite start temperature (Ms) and ends at approximately the martensite finish temperature (Mf). Upon heating, the alloy begins to return to its learned shape at the austenite start temperature (As) and finally reaches its learned shape at approximately the austenite finish temperature (Af). The transformation also exhibits hysteresis in that the transformation on heating and on cooling does not overlap. The temperature difference between Mf and Af can be designed to be as small as 10° C.

This temperature induced change is also represented in the stress-strain diagram in (a) of FIG. 3. Beginning in its base state or martensite form, the sample undergoes shape recovery, that is, it returns to its learned shape as it reverts to austenite in response to a rise in temperature to Af. Note that as temperature is then reduced back to Mf (dashed line), the sample reverts to martensite but without significant departure from the learned shape.

Normally on cooling, the martensite forms at Ms under no stress. But in the same material, martensite can form above Af if a stress is applied, and the martensite so formed is termed stress-induced martensite (SIM). The driving force for the transformation is now mechanical instead of thermal. Pseudoelasticity occurs when such a material is deformed above the Af temperature. Martensite so formed is unstable, reverting to austenite when stress is relieved. In (b) of FIG. 3 is a pseudoelastic stress-strain curve for a shape memory effect alloy. The substantially horizontal upper plateau corresponds to the formation of martensite under stress (learned shape to deformed shape) while the substantially horizontal lower plateau represents the reversion of the SIM (deformed shape to learned shape) when the stress is released. On the other hand, no such shape recovery is found in the austenite phase when the temperature exceeds the martensite by deformation temperature Md ((c) of FIG. 3), which exhibits much higher yield and flow stresses.

Tension member 26 comprising a shape memory effect alloy advantageously provides a substantially constant compressive stress in returning to its learned shape, as depicted in (a) and (b) of FIG. 3. Thus, tension member 26 having the stress-strain characteristics, as depicted in (a) and (b) of FIG. 3, can dependably apply a constant compressive force across tissue boundary 24 to promote healing, while still allowing for some expansion.

Figure 9:
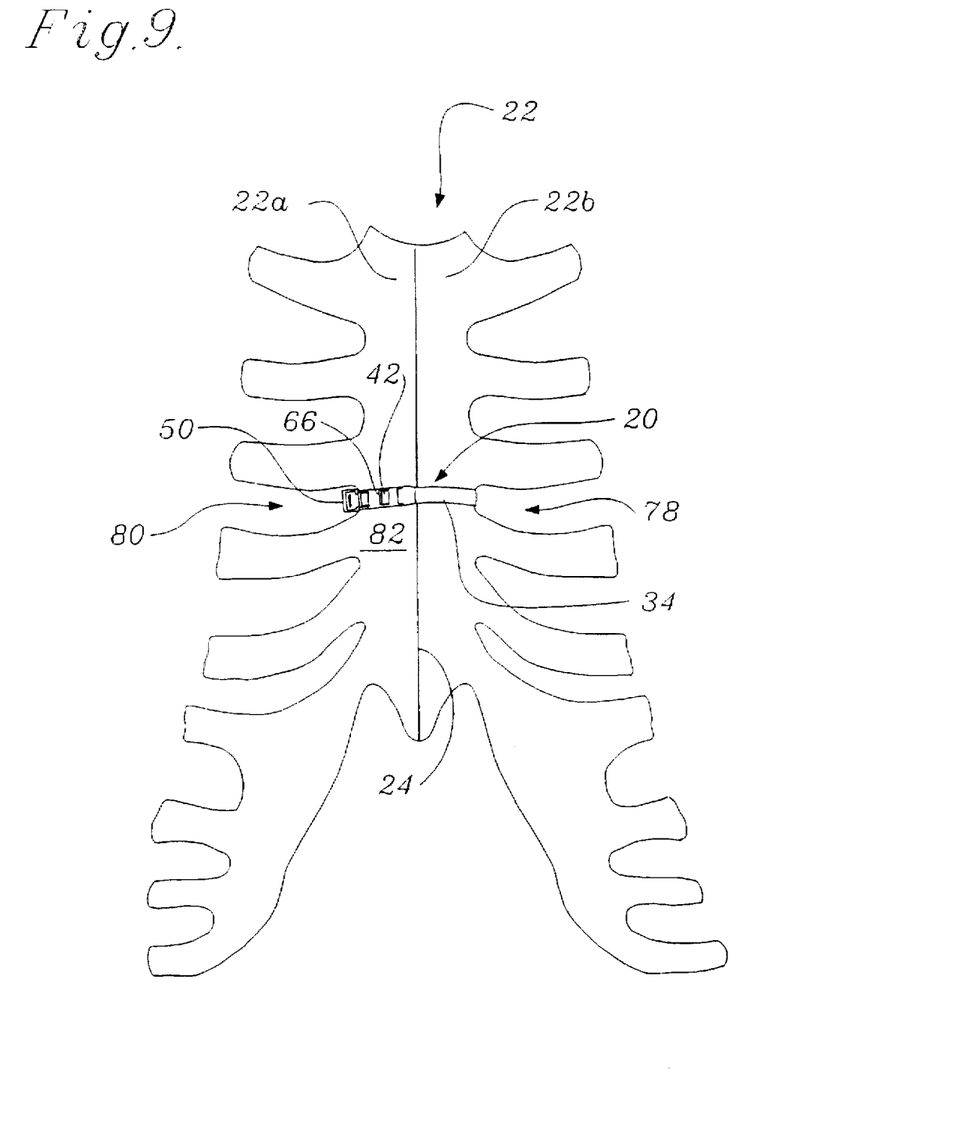
FIG. 9 is a top view of a binding device according to the present invention applied to a split sternum.

The application of binding device 20 is similar to that of a tie wrap and is illustrated fixing the halves 22a, 22b of a split sternum 22 in FIGS. 2 and 9. Needle 38 and tie portion 34 are guided in the posterior direction through a left intercostal space 78, under the posterior surface of the split sternum 22, and in the anterior direction through the corresponding right intercostal space 80. Needle 38 is then cut from binding device 20 with any of various cutting devices commonly available in a standard surgical operating room so that tie portion 34 can be pushed through cavity 52 in base 32. Tie portion 34 is then pulled further so that binding device 20 forms a slightly snug loop around the split sternum 22. Head 50 is positioned (i.e., nests) in the right intercostal space 20. Contacting teeth 57 lie against the anterior sternal surface 82 to increase friction that resists slipping movement.

A strap tightening and severing tool, such as described in U.S. Pat. No. 3,993,109 to Fortsch, may then be used to pull binding device 20 tight around sternum 22 while, as a consequence, stretching connecting member 68 essentially to point 30 of the stress-strain curve in (b) of FIG. 3. Teeth 60 of locking mechanism 58 interlock with ridges 48 to fix tie portion 34 with respect to base 32. Limit tabs 42 mate into limit holes 66 to insure that binding device 20 and connecting member 68 are not over-stressed as the binding device is tightened around the split sternum 22. As binding device 20 is tightened to its limit, that is, connecting member 68 is stretched essentially to point 30 of the stress-strain curve in (b) of FIG. 3, color stripe 47 becomes visible on tie portion 34 as a visual cue for the physician that the binding device 20 is properly tightened. The user then cuts the excess of tie portion 34 flush with base 32. The split sternum 22 experiences continuous, substantially constant, pressure as connecting member 68 attempts to contract to a shorter length along a stress-strain curve depicted in (b) of FIG. 3.

Thus, the binding device 20 advantageously applies a substantially constant compressive force across tissue boundary 24 while being able to accommodate some expansion by following the stress-strain curve beyond point 30 in (b) of FIG. 3. The binding device 20 predictably controls the maximum force that tissue in intimate contact with the device experiences. The device stretches within a desired range at a known or programmable force level, effectively resists stretching beyond that range and then is capable of returning to its prestretched length while generating a known constant force. The ability of binding device 20 to allow a limited expansive force moderates local forces in the tissue around the binding device, decreasing the likelihood of damaging or tearing the tissue.

In view of the limited range of motion, it would be possible to form the tension member 26 as a conventional spring or elastic member selected to have a relatively low spring constant (K). A low spring constant will minimize the range of force applied by the tension member over a narrow range of motion. Although not as effective as using a shape memory effect alloy, a low spring constant spring member may still provide the needed "substantially" constant tension for the strap 28.

After reading the foregoing specification, one of ordinary skill in the art will be able to make various changes, substitutions of equivalents and various other aspects of the invention as broadly disclosed herein. For example, tension member 26 may be formed integral with strap 28. The strap 28 may not be formed as a loop but instead have either end thereof attached directly to the two members to be bound or joined together. The device 20 may further have application outside of the surgical field such as bundling material which shrinks after wrapping. Base 32 or strap 28 may be formed from a shape memory effect alloy, thus eliminating the need for connecting member 68 and anchors 70, 72. It is therefore intended that the protection granted hereon be limited only by the definition contained in the appended claims and equivalents thereof.

I claim:

1. A binding device comprising:

a strap;

a one-way locking mechanism for securing said strap in the form of a loop; and a tension member attached to said strap, wherein said tension member maintains a substantially constant predetermined tension level within said strap.

2. A binding device comprising:

a strap; and a tension member attached to said strap, wherein said tension member maintains a substantially constant predetermined tension level within said strap, wherein said tension member is a pseudoelastic shape memory effect alloy.

3. A binding device as recited in claim 2, wherein said shape memory effect alloy is selected from the group consisting of nitinol, Cu-Zn-Al and Cu-Al-Ni.

4. A binding device as recited in claim 3, further comprising a one-way locking mechanism for securing said strap in the form of a loop.

5. A surgical binding device for binding tissue, said binding device comprising:

a strap adapted to be positioned across adjacent edges of tissue and tightened for holding the tissue in close proximity; and a tension member attached to said strap wherein said tension member is a pseudoelastic shape memory effect alloy which maintains a substantially constant predetermined tension level in said strap, said shape memory alloy including stable austenite below martensite deformation temperature (Md).

6. A surgical binding device as recited in claim 5, wherein said strap comprises a frictional surface for contacting the tissue and preventing translation therebetween.

7. A surgical binding device as recited in claim 5, wherein said shape memory effect alloy is selected from the group consisting of nitinol, Cu-Zn-Al and Cu-Al-Ni.

8. A surgical binding device as recited in claim 5, wherein said strap is provided with a piercing end for insertion through the tissue.

9. A surgical binding device as recited in claim 8, wherein said piercing end is a removable needle.

10. A surgical binding device for binding tissue, said binding device comprising:

a strap adapted to be positioned across adjacent edges of tissue and tightened for holding the tissue in close proximity, wherein said strap is provided with a piercing end for insertion through the tissue and has a base opposite said piercing end and a tie portion, said base adapted to irreleasably receive said piercing end and said tie portion to form a tightenable loop; and a tension member attached to said strap wherein said tension member maintains a substantially constant predetermined tension level in said strap.

11. A surgical binding device as recited in claim 10, further comprising a limiting mechanism for limiting the force applied to said tension member when said strap is tightened.

12. A surgical binding device as recited in claim 11, wherein said limiting mechanism comprises limiting tabs on one end of said tie portion and limiting holes on one end of said base, wherein said limiting tabs coact with said limiting holes to limit movement of said tie portion relative to said base.

13. A surgical binding device comprising:

a base and a locking member;

a strap adapted to form a loop for holding tissue in close proximity; and a tension member connecting said base to said strap, wherein said tension member maintains a substantially constant tension in said loop.

14. A method of binding together injured tissue under a compressive force to promote healing, comprising the steps of:

(a) drawing together in close proximity opposing edges of injured tissue by tightening a strap which forms a loop about the injured tissue; and (b) tightening said strap so that a tension member within said strap exerts a substantially constant tension within said loop to maintain the tissue in close proximity.

* * * * *

UNITED STATES PATENT AND TRADEMARK OFFICE
CERTIFICATE OF CORRECTION

PATENT NO. : 5,766,218
DATED : June 16, 1998
INVENTOR(S) : Richard J. Arnott

It is certified that error appears in the above-identified patent and that said Letters Patent is hereby corrected as shown below:

In the Drawings, Drawing Sheet 2 of 5, refer to Fig. 3, "A1" should read --Af--.

Signed and Sealed this

Fifth Day of January, 1999

Attest:

*Attesting Officer*

*Acting Commissioner of Patents and Trademarks*